(12) United States Patent  (10) Patent No.: US 8,036,734 B2
Schmidt  (45) Date of Patent: Oct. 11, 2011

(54) METHOD FOR DETERMINING CARDIAC IMPULSE CONDUCTION AND ASSOCIATED MEDICAL DEVICE

(75) Inventor: Sebastian Schmidt, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 685 days.

(21) Appl. No.: 12/069,167

(22) Filed: Feb. 7, 2008

(65) Prior Publication Data

US 2008/0200822 A1 Aug. 21, 2008

(30) Foreign Application Priority Data

Feb. 15, 2007 (DE) .......................... 10 2007 007 563

(51) Int. Cl.
*A61B 5/0402* (2006.01)
(52) U.S. Cl. ........ 600/512; 600/508; 600/509; 600/513; 600/523; 382/128; 382/130; 128/920; 128/922
(58) Field of Classification Search .......... 600/508–509, 600/512–513, 523; 382/128, 130; 128/920, 128/922
See application file for complete search history.

(56) References Cited

U.S. PATENT DOCUMENTS

| 5,637,090 A * | 6/1997 | McGee et al. ................ 600/374 |
| 6,600,948 B2 * | 7/2003 | Ben-Haim et al. ............ 600/512 |
| 2004/0082870 A1 | 4/2004 | Ghanem |
| 2006/0241518 A1 | 10/2006 | Boese et al. |
| 2007/0073179 A1 * | 3/2007 | Afonso et al. ................ 600/523 |

FOREIGN PATENT DOCUMENTS

DE 192005005037 A1 8/2006

* cited by examiner

*Primary Examiner* — Carl H Layno
*Assistant Examiner* — Deborah Malamud

(57) ABSTRACT

A method for determining cardiac impulse conduction, in particular three-dimensional cardiac impulse conduction, in a patient, comprising: generating an image recording of an area of the body of the patient capturing at least partially electrocardiogram electrodes arranged on the body of the patient by an imaging modality; determining positions of the electrocardiogram electrodes in a system of coordinates assigned to the imaging modality; recording of potential data of some of the electrocardiogram electrodes; and reconstructing cardiac impulse conduction depending on the determined positions of the electrocardiogram electrodes, the image recording and the recording of potential data of the electrocardiogram electrodes, wherein at least one image recording is generated substantially simultaneously with the recording of potential data of the electrocardiogram electrodes or is generated in the period between two recordings of potential data of the electrocardiogram electrodes.

19 Claims, 2 Drawing Sheets

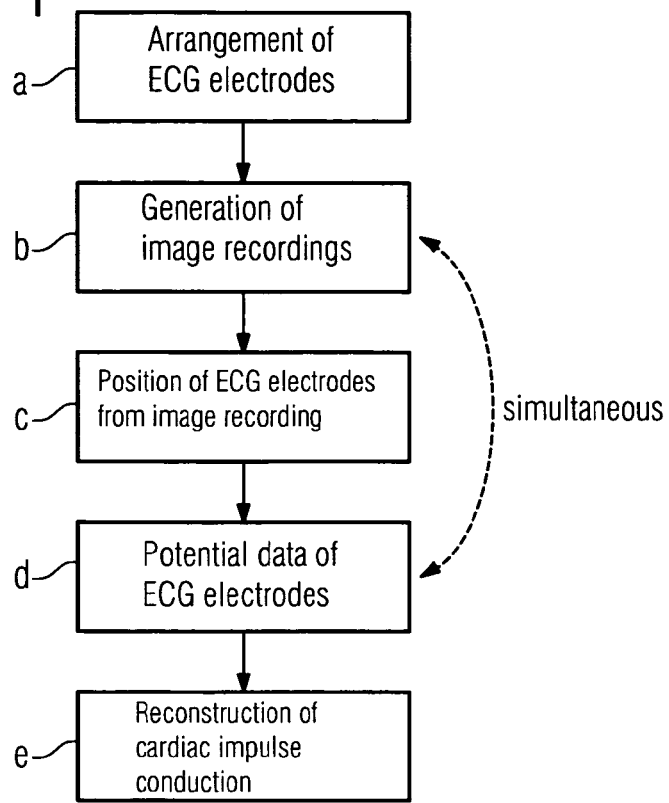
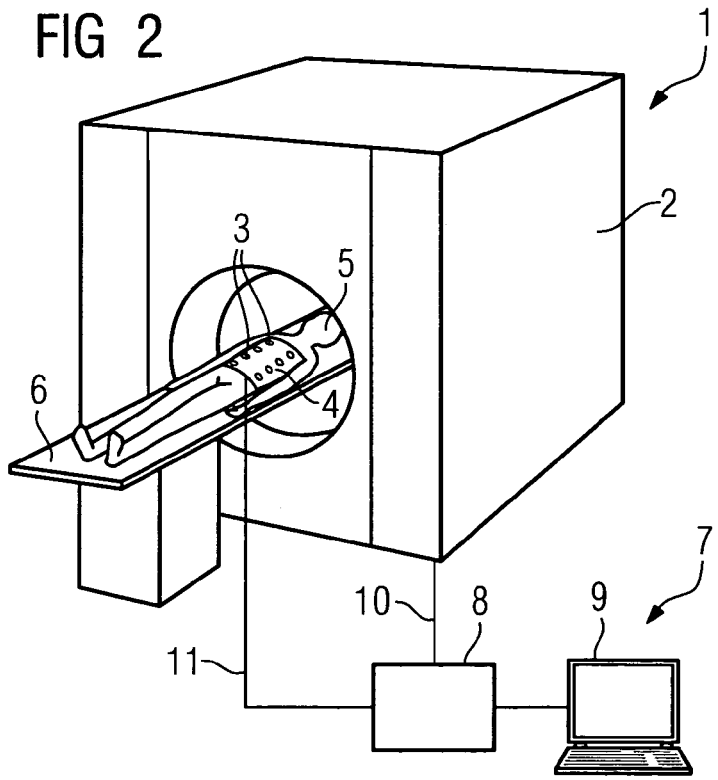

METHOD FOR DETERMINING CARDIAC IMPULSE CONDUCTION AND ASSOCIATED MEDICAL DEVICE

CROSS REFERENCE TO RELATED APPLICATIONS

This application claims priority of German application No. 10 2007 007 563.6 filed Feb. 15, 2007, which is incorporated by reference herein in its entirety.

FIELD OF THE INVENTION

The invention relates to a method for determining cardiac impulse conduction, in particular for determining three-dimensional cardiac impulse conduction, in a patient and to an associated medical device for determining cardiac impulse conduction.

BACKGROUND OF THE INVENTION

In numerous disorders in the area of cardiology, for example in a case of myocardial infarction or in cases of cardiac arrhythmia, the propagation of electrical signals in the heart is altered. This results in a change in the electric field of the heart, the sum vector of which is evident in changes in the electric potentials on the body surface of a patient.

In an electrocardiogram (ECG), the electric potentials and/or the changes in the electric potentials at the body surface of the patient are captured, in order to draw conclusions therefrom as to the propagation of electric excitation in the heart and/or as to the electric field of the heart. The changes of potential are represented over time as curves in order in this way to enable a doctor subsequently to diagnose disorders.

In a conventional ECG, assessment of cardiac impulse conduction is restricted, however, as the electrodes even in a 12-channel ECG are not arranged in all planes, so that propagations of the electric field which have a vector perpendicular to the planes captured are not captured. This problem can be partially solved by increasing the number of electrodes. As a result of this, however, diagnosis becomes increasingly difficult as the number of curves is very high and these are ultimately difficult to interpret so that highly trained specialists are required to assess them.

Rather than recording the changes of potential at the body surface of the patient as individual curves, it is therefore advantageous actually to record the propagation of impulse conduction in the heart, i.e. the corresponding sum vector itself. It would in this way be significantly easier in a subsequent diagnosis to detect cardiac disorders and to plan a treatment.

A representation of this type is referred to as a "vector cardiogram", and it has been possible for it to be determined in the research field, for example, in the isolated beating heart. In a living patient, the reconstruction of such a vector cardiogram is possible only with very great difficulty as the currently existing solutions are associated with considerable costs.

For example, DD 284 594 shows a device for deriving cardiac potentials, in which the electrodes are brought into position by means of mechanical positioning aids. The position of these positioning aids is then measured and this information utilized.

The reason why the currently existing methods for the reconstruction of vector cardiograms are very costly and of limited practicability, is that, in order to reconstruct the propagation of excitation of the heart on the basis of the measured potentials, the precise position of the electrodes used and the anatomy, i.e. in particular the shape of the heart, have to be known.

The publication US 2004/0082870 A1 relates to systems and methods for determining a surface geometry of an object, providing for the determination of a first projection matrix based upon a first imaging device, the determination of a second projection matrix based upon a second imaging device, the recording of at least one first two-dimensional image of the object using the first imaging device and the recording of at least one second two-dimensional image of the object using the second imaging device and the determination of a contour of the object in the first two-dimensional image and the second two-dimensional image. Taking the at least two contours, the first projection matrix and the second projection matrix as a basis, the aim is to reconstruct three-dimensional data which relates to the surface of the object, which may be the heart of a patient. Where a vest with electrodes is used, the torso geometry and thereupon the positions of the electrodes can be determined from image data. In addition, the electric potentials at the body surface can be measured with the aid of the electrodes of such a vest.

SUMMARY OF THE INVENTION

The object of the invention is thus to indicate an improved method in this regard for determining cardiac impulse conduction, in particular three-dimensional cardiac impulse conduction, in a patient.

In order to achieve this object, such a method comprising the following steps is provided:
- generation of at least one image recording of at least one area of the body of the patient, which image recording captures at least partially electrocardiogram electrodes arranged on the body of the patient, by means of at least one imaging modality,
- determination by a computing device of the positions of the electrocardiogram electrodes captured in the image recording, in a system of coordinates assigned to the imaging modality, directly on the basis of the image recording,
- recording of potential data of at least some of the electrocardiogram electrodes captured in the image recording and
- depending on the determined positions of the electrocardiogram electrodes, the at least one image recording and the at least one recording of potential data of the electrocardiogram electrodes, reconstruction of cardiac impulse conduction by the computing device, wherein at least one image recording is generated at least substantially simultaneously with the recording of potential data of the electrocardiogram electrodes and/or wherein at least one image recording is generated in the period between two recordings of potential data of the electrocardiogram electrodes.

Thus, according to the invention, firstly ECG electrodes are arranged on the body of the patient, a matrix of ECG electrodes advantageously being chosen. Here, the number or arrangement of the electrodes is designed such that the major part of the upper body of the patient is captured by means of the electrodes.

Subsequently, at least one image recording of at least one area of the body of the patient, i.e. advantageously of an area of the upper body or of the thorax or of the entire upper body, which is covered with electrocardiogram electrodes, is generated by means of an imaging modality or by means of a plurality of imaging modalities. The image recording can be an image recording composed from the image data of a plurality of different modalities or an image recording for which only image data of one modality has been used. Advantageously, all the electrodes arranged on the body of the patient are detectable in the image recording.

In selecting the imaging modality, care must be taken to ensure that the electrocardiogram electrodes in the image recording are detectable or that the image recording method is compatible with the ECG electrodes.

On the basis of the image recording, the positions of the electrocardiogram electrodes captured in the image recording are determined at least partially by a computing device. The position determination is usefully effected such that the coordinates in a system of coordinates which is assigned to the imaging modality are indicated. In principle, the system of coordinates is arbitrarily selectable. According to the invention, the position of the ECG electrodes is determined directly on the basis of the image data, i.e. directly on the basis of the ECG electrodes which can be seen in the image recording, e.g. by means of software comprising image processing routines. In this sense, the electrode position is determined immediately on the basis of the image recording of the imaging modality, i.e. for example a magnetic resonance image recording.

In addition, according to the invention, the potential data of at least some, preferably all, of the electrocardiogram electrodes captured in the image recording are recorded. This can, for example, occur simultaneously or substantially simultaneously with the generation of the image recording by means of the imaging modality.

Depending on the determined positions of the electrocardiogram electrodes, the at least one image recording and the at least one recording of potential data of the electrocardiogram electrodes, cardiac impulse conduction is reconstructed or computed by the computing device, which has suitable computer design software, or has access to such software, for this purpose. The influence exerted by the tissue, in particular an enveloping tissue or a tissue surrounding the heart, can be extracted from the image recording or the plurality of image recordings.

The method can at least in part be carried out automatically by the computing device, it optionally being possible for monitoring by technical personnel or an engineer or natural scientist, in particular a physicist, to be provided. The technician or natural scientist can optionally specify, via an image outputting means of the computing device, certain specifications for the image recording or the recording of potential data by the ECG electrodes or the reconstruction of cardiac impulse conduction on the basis of the recorded measurement data. The arrangement of the electrocardiogram electrodes, which is shaped by physical considerations, can also be undertaken by technical personnel. Alternatively, appropriately trained medical personnel can be deployed.

Through direct determination of the positions of the ECG electrodes from the image recording or the image recordings, electrode capture and/or detection is possible without additional conversion procedures. It is thus no longer necessary to carry out a complicated conversion or transformation which is based on image recordings produced previously or independently of the ECG recording and which possibly do not show the electrodes at all or not in the currently correct position for the ECG recording.

According to the invention, at least one image recording is generated at least substantially simultaneously with the recording of potential data of the electrocardiogram electrodes and/or in the period between two recordings of potential data of the electrocardiogram electrodes. A recording of the image data, i.e. for example magnetic resonance tomography data, is therefore carried out particularly advantageously during the measurement of the ECG data. This makes it possible to determine the propagation of electric excitation in the heart through a combination of directly corresponding ECG data and magnetic resonance tomography data. The ECG data here supplies the information about the electric potentials at the body surface of the patient, while the magnetic resonance tomography data indicates the shape or anatomy of the heart, the thorax and the position of the electrodes, or this can be derived from this data.

The ECG recording can be carried out continuously or at short time intervals, while the magnetic resonance recordings or recordings by means of a different imaging method are generated simultaneously, for which purpose defined recording sequences or recording successions can be used.

Through the image recording, the anatomy, i.e. in particular the position of the heart and the shape of the thorax, is captured, while simultaneously, through determination of the position of the electrocardiogram electrodes, the electric potentials at the body surface of the patient can be assigned in a spatially accurate manner.

According to the invention, at least one image recording can be generated triggered by the recording and/or evaluation of potential data of the electrocardiogram electrodes and/or image recordings can be generated as part of image sequences, in particular of very rapid image sequences. This enables effective simultaneous recording of the potentials of the electrodes and of the magnetic resonance data or other data of another imaging method. As a result of the triggering, in particular the ECG triggering, possible motion blur is minimized. Furthermore, very rapid sequences enable a high temporal resolution for the image recording.

A magnetic resonance device and/or a computer tomography device and/or a different X-ray-based device can be used as an imaging modality. The image recordings can optionally be combined from data of various image recording methods. For example, recordings in which the position of the electrocardiogram electrodes can be detected particularly well can be produced with a magnetic resonance device, while further information is obtained from X-ray recordings.

A key factor in the selection of the imaging modality or a combination of imaging modalities is ultimately the question of whether the shape of the heart and of the thorax and the position of the electrodes used can be determined sufficiently well or accurately therefrom.

From the at least one image recording, a three-dimensional model, in the case of multiple image recordings in particular a temporally resolved three-dimensional model, of the thorax can be determined. This three-dimensional model of the thorax can subsequently, for example by means of automatic image processing, be further processed in order to detect the areas of interest or to pinpoint the positions of electrodes. If a plurality of image recordings are generated, for example as part of a rapid recording sequence or a film, then a three-dimensional model of the thorax can be determined in a temporally resolved manner therefrom which takes into account cardiac and respiratory movement and which can then also serve as a foundation for determining the three-dimensional propagation of impulse in the heart of the patient.

According to an embodiment of the invention, the heart and/or the surface of the thorax and/or the spatial position of the electrocardiogram electrodes can be determined in the three-dimensional model of the thorax automatically by a, or the aforementioned, computing device, in particular by means of at least one segmentation method.

For this purpose, an appropriate item of software is available on the computing device, or this computing device can access an appropriate item of software or a software package of another computing device or of an external storage medium, which software or software package enables tissue segmentation. The shape of the heart and/or the heart as such can in this way be pinpointed and detected, as can the body surface of the patient. The segmentation method can, with the aid of suitable pattern recognition methods and by drawing on anatomical libraries, operate fully, or to a large extent, automatically. Supportive interventions of an operator are optionally possible. For example, said operator can choose predetermined parameters for the segmentation.

Furthermore, from the at least one image recording or the plurality of image recordings, a three-dimensional model can be generated in which the tissues are segmented and electrical properties assigned to these. In the case of multiple image recordings in a defined time sequence, this model can in turn be generated in a temporally resolved manner. The tissue segmentation and the assignment of electrical properties form the basis for determining impulse propagation in the heart of the patient. The three-dimensional model with the segmented tissue components and electrical properties assigned to these components can be based on a three-dimensional model of the thorax, which has optionally been determined in advance.

Cardiac impulse conduction can be reconstructed by means of the three-dimensional model. The segmentation allows differentiation between different tissues, the assignment of electrical properties enabling a targeted forecasting or computation of the influence of an electric field and thus of the propagation of excitation.

Cardiac impulse conduction can be reconstructed according to the invention particularly advantageously in the form of a vector cardiogram, in particular a three-dimensional vector cardiogram. A vector cardiogram of this type advantageously represents the propagation of impulse conduction in the heart as a three-dimensional sum vector. This makes it possible in a subsequent diagnosis in an effective manner to detect disorders such as cardiac arrhythmias and the like and to plan a treatment.

The reconstructed cardiac impulse conduction can be visualized by a computing device, optionally by means of the computing device which has already carried out the segmentation and determination of the position of the electrodes, in particular on an image outputting means of the computing device, together with the at least one image recording. Here, the single or multiple image recordings can be represented adjacent to or alongside a representation of the reconstructed cardiac impulse conduction, in particular in the form of a vector cardiogram. This can optionally take place using shared visualization software. It is also possible for the reconstructed cardiac impulse conduction to be integrated or inscribed directly into a representation of the anatomy such that a direct assignment of the impulse conduction to the underlying anatomical structure or to further image data which can be detected from the image recording or the film of image recordings is possible. Optionally, a joint or separate representation of cardiac impulse conduction and of the image recording can be initiated by an operator or by means of a presetting in a single graphical representation or in succession.

The reconstructed cardiac impulse conduction is visualized particularly advantageously in the image recording in color and/or in an optically highlighted manner. For example, the 3D-vector cardiogram determined can be inscribed or integrated in color, optionally using multiple colors, in a magnetic resonance image consisting of gray levels, or can be superimposed upon this. In addition, a further optical highlighting can be implemented, for example a flashing or a tracing of particularly broad lines or a conspicuous outline marking.

The visualization can be effected by the computing device depending on a user input and/or temporarily. The technician or natural scientist, optionally also a doctor, controlling the ECG recording or the image recording, e.g. with the aid of a magnetic resonance tomograph, can thus input in advance that the visualization should take place at intervals of a few seconds and/or depending on the cardiac cycle or depending alternately on impulse conduction data and image data. Furthermore, a visualization may from the outset be provided only at specified times. For example, in a time-resolved recording of heart movement in real time, among other things by means of a so-called "cine" method or the like, a visualization may occur only at specified times, for example in each nth cardiac cycle.

By means of the imaging modality, image recordings can be generated in a time-resolved manner over at least a part of one or more cardiac cycles. In this way, a recording and representation of the anatomy over a longer time period, in particular a complete cardiac cycle, can be achieved. A time-resolved image recording which enables tracing of the cardiac cycle in real time is particularly advantageous.

From the image recordings a film can be generated, in particular a film in which cardiac impulse conduction is visualized. In this case, not only can the anatomy of the beating heart or of a surrounding area be traced over a complete cardiac cycle or even several cardiac cycles in the manner of a three-dimensional film, but also the propagation of electrical excitation in the heart of the patient. This enables a doctor, to whom the data, processed in this manner, is displayed by the computing device automatically or with the cooperation of a technician or natural scientist, to make a reliable and simple diagnosis. It is at the same time also conceivable to alternate between the representation of a film and the representation of a recorded image, on which cardiac impulse conduction can be superimposed in each case, for example automatically or depending on settings specified by an operator in advance.

For capturability by means of and/or detectability in the at least one image recording, the electrocardiogram electrodes can each be provided with at least one marking. The markings are chosen with a particularly advantageous effect such that they are especially readily visible in the respective image recording method. For different electrocardiogram electrodes different markings or markers can optionally be used, in particular in such a way that respectively adjacent electrodes exhibit different markers or types of marking so as to enable improved identification of the individual electrodes. In order to additionally secure the determination of positions on the basis of markers, multiple markers can optionally be used for individual electrodes. This is conceivable, for example, where specially marked electrodes are used at anatomically relevant points or the like.

The electrocardiogram electrodes can be provided with a marking composed of a material having a unique contrast behavior, in particular a metal material, and/or a resonance coil and/or a fluorescent marker and/or an X-ray marker. A unique contrast behavior of a material means that this material stands out well in the image recording. Optionally, markers can be used which are different from those mentioned, e.g. if, with different markers, the respective imaging modality enables better and more accurate identification of the electrodes. Multiple markers can be cumulatively applied to individual electrodes, it also being possible for a selection of the markers to be made depending on the respective locations or positions of the electrodes, in particular with regard to special identification difficulties.

The positions of the electrocardiogram electrodes can be determined taking into account a known relative position of the electrocardiogram electrodes to one another and/or with the aid of markings deviating at least partially from one another on the electrocardiogram electrodes for identifying the individual electrocardiogram electrodes. The use of different markings and of a known arrangement of individual ECG electrodes relative to one another, for example known neighborhood relations, optionally in combination, makes it possible to identify the electrodes individually, thereby ultimately ensuring or enabling reliable position detection and/or monitoring of position detection.

Furthermore, the markings in the at least one image recording can deviate from one another in terms of their signal strength and/or signal length and/or signal type. Deviations of signal type can arise for example through the use of different marker types or principles or of different materials. The signal strength or signal length may be different simply on account of the different positions of the individual ECG electrodes and/or may from the outset be chosen such that different strengths and/or spatial extensions are produced. This can be achieved, for example where resonance coils are used, through different embodiments for example with regard to the number of windings and/or the spatial extension and the cross-sectional area.

The electrocardiogram electrodes can be arranged in a matrix form and/or on a vest, in particular on a vest that is flexible and/or tight-fitting on the body of the patient. The matrix form of the ECG electrodes offers the advantages that each electrode has a defined number of neighbors, which advantageously have constant or at least defined distances from one another. In a particularly practical embodiment, a matrix arrangement can be implemented as a vest which the patient pulls on for the recording of the ECG and the image recording. Such vests are advantageously fashioned flexibly such that they adapt to or fit tightly the upper body of the patient. Alternatively, individual electrodes can also be connected to one another to form a matrix by means of suitable, in particular flexible, materials.

50 to 200 electrocardiogram electrodes, for example, can be arranged on the body of the patient. By means of such a number of electrodes, the major part of the upper body can be captured. Different numbers of electrodes are, however, also conceivable, depending on how accurately cardiac impulse conduction is to be reconstructed or what form an underlying diagnostic problem takes.

Advantageously, the measurement signals of the electrocardiogram electrodes can be transmitted at least in part wirelessly and/or using optical waveguides. This enables an improved compatibility in the measurement of the potentials of the electrodes, in particular with regard to the generation of magnetic resonance image recordings. Optionally, the two transmission methods can be combined, for example for one and the same electrode, or different methods of signal transmission can be used for different electrodes, thereby simplifying identification of the electrodes.

In addition, the invention relates to a medical device for determining cardiac impulse conduction, comprising at least one imaging modality and comprising electrocardiogram electrodes and means for determining the potentials applied to the electrocardiogram electrodes and comprising at least one computing device, preferably with an image outputting means, configured for implementing the method as described hereinabove.

The medical device is thus configured such that, through a combination of ECG data and data of an imaging device, for example a magnetic resonance device, the information about the electric potentials at the body surface of a patient can be acquired simultaneously with image data which provides the shape or anatomy of the heart and of the thorax and the position of the electrodes. The acquisition of all the information that is necessary for a comprehensive reconstruction of the propagation of excitation in the heart of the patient, in particular as a 3D-vector cardiogram, is thus made possible, in particular through a simultaneous or ECG-triggered recording of potential data and image data.

For this purpose, the ECG electrodes are arranged on the body of the patient, and by means of the imaging modality an image recording, for example a magnetic resonance recording, is generated with which it is possible to detect the ECG electrodes, which have, for example, markers for this purpose. The positions of the electrocardiogram electrodes are determined directly from the image recording. Simultaneously or subsequently, the potential data, for example for the same part of the heart, is recorded. Depending on the positions of the ECG electrodes determined and on the anatomical data of the image recording and depending on the recording of potential data, a reconstruction of cardiac impulse conduction, for example in the form of a three-dimensional vector cardiogram, can be carried out by the computing device.

To this end, the computing device advantageously has a suitable software means or the computing device can access a software means or a software package on an external computing device or a storage medium, which comprises among other things image processing means enabling tissue recognition and assignment or segmentation. This software can subsequently also be configured for reconstructing cardiac impulse conduction, for example by means of an add-on software package with corresponding computational functions.

At least one imaging modality of the device can be a magnetic resonance device and/or a computer tomography device and/or another X-ray-based device. Various imaging modalities can optionally be combined in the medical device, for example in order to obtain, through different and complementary recording methods, an optimum representation of the anatomy. Further imaging methods not mentioned here may also be present, for example an ultrasound device, in order to provide further image recording possibilities.

The computing device is usefully fashioned for determining the positions of the electrocardiogram electrodes captured in the image recording directly on the basis of the image recording and for reconstructing cardiac impulse conduction depending on the determined positions of the electrocardiogram electrodes, the at least one image recording and the at least one recording of potential data of the electrocardiogram electrodes, in particular by means of software available on the computing device and/or externally. The computing device thus has a software means stored on an internal or external memory, which, using pattern recognition or a similar method, optionally taking into account a known relative arrangement, captures the positions of the ECG electrodes and computes or determines cardiac impulse conduction, drawing on anatomical information obtained from the image recording, in particular with regard to the influence of tissue. The computing device can, for the purposes of positional determination or of reconstruction of cardiac impulse conduction, optionally fall back on external software, for example on a central server or a server of a service provider. An appropriate data connection has to be provided for this purpose.

In addition, the computing device can be configured for controlling the recording of potential data of the electrocardiogram electrodes and/or for controlling the image recording with the imaging modality and/or for image recording with the imaging modality triggered by the recording and/or evaluation of potential data of the electrocardiogram electrodes, in particular by means of software available on the computing device and/or externally.

The computing device, which determines the positions of the electrocardiogram electrodes, consequently also controls the recording activity with regard to the measurement of potential data or the image recording with the imaging modality. In this sense, the computing device thus simultaneously functions as controller for ECG generation and for image recording. To this end, the computing device may consist of a plurality of individual computing components to which different housings or screens or such like are optionally assigned. The computing device may, however, also be an integrated computer which simultaneously serves to control and carries out the evaluation of the recorded data.

In a particularly advantageous embodiment, the computing device is configured such that, in cases where it controls the image recording, it does so triggered by the ECG. This triggering can take the form whereby the recording of the potential data occurs simultaneously with the image recording or whereby the potential data is evaluated with regard to a corresponding phase of the cardiac cycle or such like, whereupon the image recording is started.

Furthermore, the computing device can be configured for visualizing the reconstructed cardiac impulse conduction by means of representation on an image outputting means. In particular, it can be configured for representing the reconstructed cardiac impulse conduction together with the at least one image recording. The image recording or a film of image recordings can consequently be represented on a monitor or flat screen or such like, the reconstructed cardiac impulse conduction also being input by the computing device into the representation, for example in the form of the three-dimensional vector cardiogram. This can be done, for example, by overlaying the two image representations, it being possible for the vector cardiogram or another representation of the reconstructed cardiac impulse conduction to be highlighted in color, for example. The representation can also be effected jointly in a manner such that respectively matching anatomical image recordings are represented on the one side and the associated computed cardiac impulse conduction on the other simultaneously in different images adjacent to one another or are shown in different areas of an integrated representation. A separate representation is also possible.

The electrocardiogram electrodes of the medical device may each have at least one marking which can be detected in image recordings by the imaging modality, it being possible for the marking concerned to be, for magnetic resonance image recordings, a material having a unique contrast behavior such as metal or a resonance coil and such like.

All in all, it is possible by means of the medical device according to the invention to determine cardiac impulse conduction in particular three-dimensionally, i.e. to record the sum vector of impulse conduction in the heart so as to enable a doctor subsequently to make an optimum diagnosis on the basis of this measured data.

BRIEF DESCRIPTION OF THE DRAWINGS

Further advantages, features and details of the invention will emerge from the exemplary embodiments below and from the drawings, in which:

FIG. 1 shows a flow diagram of a method according to the invention,

FIG. 2 shows a medical device according to the invention,

DETAILED DESCRIPTION OF THE INVENTION

Figure 3:
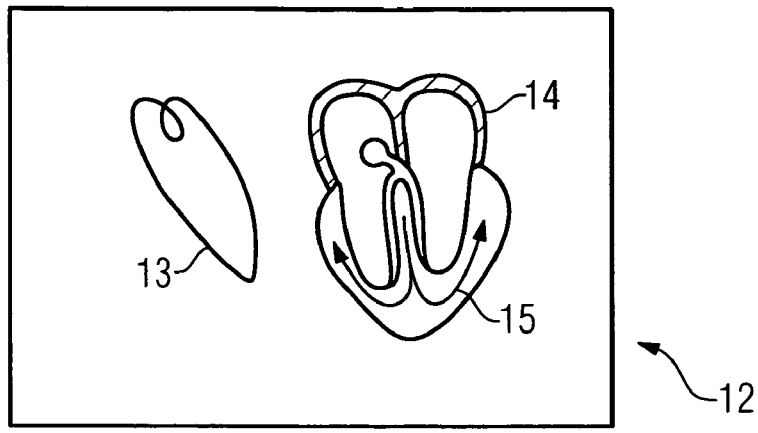
FIG. 3 and FIG. 4 show schematic diagrams of cardiac impulse conduction and of the heart in the case of a healthy heart and in the case of tissue damage due to infarction respectively and FIG. 5 shows a schematic diagram of the overlaying of an image recording and of the reconstructed cardiac impulse conduction.

FIG. 1 represents a flow diagram of a method according to the invention comprising steps a-e. Firstly, in step a, the ECG electrodes for recording the electric potentials are arranged on the upper body of the patient. Then, in accordance with step b, at least one image recording or even a film of image recordings of at least one area of the body of the patient, advantageously of the area in which the ECG electrodes are arranged, is generated. This may, for example, be carried out by means of a magnetic resonance tomograph or by means of another imaging device which records e.g. the thorax of the patient.

The positions of the ECG electrodes are, in accordance with step c, determined directly from the image recording. Consequently, not only is the anatomy, i.e. the shape of the heart and of the thorax of the patient, derived from the image recording, but the position of the electrodes is also determined therefrom.

In step d, a recording of potential data of the ECG electrodes is started. This can optionally, as indicated by the dotted arrow, take place simultaneously with the recording of the image data. If the image data, for example magnetic resonance data, is captured during the measurement of the ECG data, then the ECG data can be assigned directly to the image recordings. This dispenses with the need for a time-consuming subsequent assignment of, for example, previously recorded magnetic resonance data to a later electrode arrangement in order in this way to be able to reproduce the positions of the electrodes. The image recording can also be triggered by the ECG.

From the magnetic resonance data and the ECG data, i.e. through knowledge of the anatomy, the positions of the electrodes and the ECG potentials, the propagation of excitation in the heart can be reconstructed three-dimensionally in accordance with step e. For example, a three-dimensional vector cardiogram can be generated that is represented by a computing device on a screen.

FIG. 2 represents a medical device 1 according to the invention for determining cardiac impulse conduction, which medical device has an imaging modality 2, here a magnetic resonance tomograph. Furthermore, ECG electrodes 3 are present which are arranged in a matrix-type arrangement on a vest 4 which a patient 5 wears.

The patient 5 is located, for the recording of the ECG data and the image data, on a patient examination table 6, on which he is conveyed into the imaging modality 2. The vest 4 or the ECG electrodes 3 are controlled via a computing device 7. Besides the actual computing means 8, the computing device 7 has an image outputting means 9 which enables an operator, i.e. in particular a technician or natural scientist, (not shown here), to control the recording of the measured data with the aid of the ECG electrodes 3 or the imaging modality 2 and to process or display the finished data for a diagnosis to be undertaken by a doctor. The computing device 7 is connected via data lines 10 and 11 to the imaging modality 2 and the vest 4 and the ECG electrodes 3 respectively. The ECG data can alternatively also be transmitted wirelessly.

If the magnetic resonance data is now recorded with the aid of the imaging modality 2 during the measurement of ECG data by means of the ECG electrodes 3, then impulse conduction in the heart can be reconstructed three-dimensionally from the anatomical data of the image recording and the electrode positions to be derived herefrom in connection with the potential data. For improved detectability in the magnetic resonance tomography recording, the ECG electrodes 3 are provided with a metal marker, the markers not being shown in the representation. Determination of the position of the individual ECG electrodes 3 is simplified by their defined relative position in the vest 4. This makes it possible to identify the individual ECG electrodes 3 in the image recording which shows the upper body of the patient 5. To this end, image processing is carried out by the computing device 7 using suitable software 6 and cardiac impulse conduction then computed from this data, the potential data and the anatomy. After computation, cardiac impulse conduction is represented to an operator on the image outputting means 9 in a desired representation, i.e. for example as an overlay of the impulse conduction with an anatomical image recording.

FIG. 3 shows a schematic diagram 12 of cardiac impulse conduction 13 and of the heart 14 for a healthy heart. The arrows 15 are intended to indicate the direction of the propagation of excitation in the heart 14. In the schematic diagram 12, the image of the heart 14 is represented together with (adjacent to) the associated cardiac impulse conduction 13.

Figure 4:
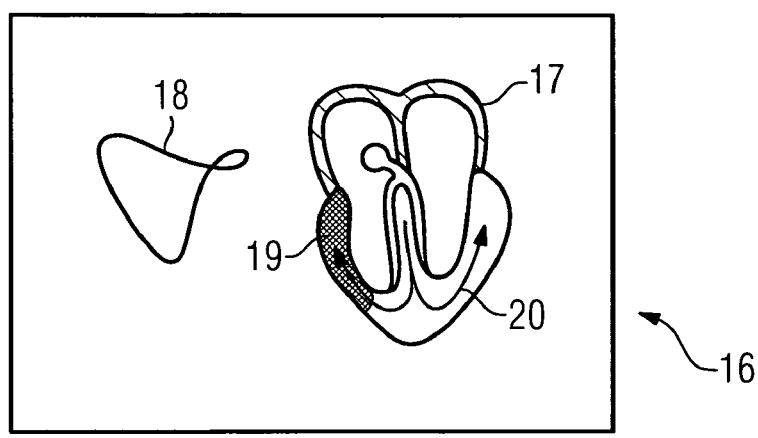

The schematic diagram 16 in FIG. 4 shows the heart 17 and the associated cardiac impulse conduction 18 for a comparable cardiac phase, i.e. at the same point in the cardiac cycle as in FIG. 3, but where there is tissue damage due to an infarction, indicated here by the dark area 19. As a result of the tissue damage, the propagation of excitation, as shown by the arrows 20, is disturbed. Accordingly, cardiac impulse conduction 18 exhibits in the vector form in which it is represented a different configuration, which makes it possible to detect, as part of the later diagnosis, that a deviation from the norm is occurring at this point in the cardiac cycle, i.e. an infarction is present or could be present in a certain area.

In this way, by means of the precise representation of cardiac impulse conduction 13, 18 in vector form, it is possible in a substantially simpler manner to directly infer the existence of damage to the heart than is possible from multiple ECG curves which have to be evaluated in combination. Less expert knowledge is thus required for diagnosis in the case of a representation of the propagation of cardiac impulse conduction than is the case with conventional ECG curves, particularly where there is a large number of recorded curves.

Figure 5:
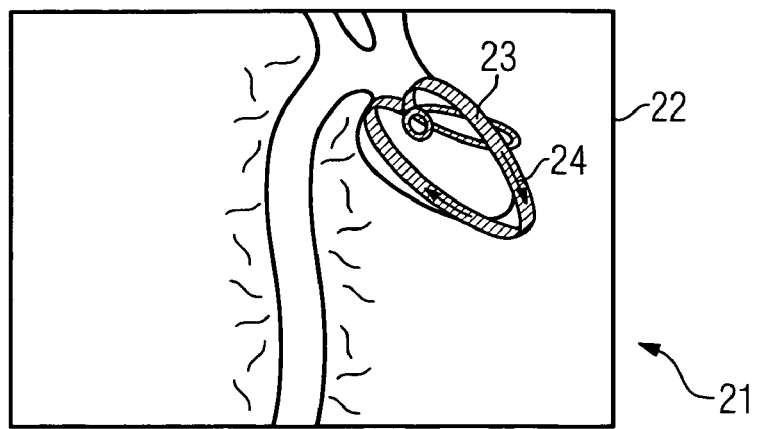

Finally, FIG. 5 shows a schematic diagram 21 of the overlaying on an image recording 22, which is a magnetic resonance recording showing the thorax, with an associated reconstructed three-dimensional cardiac impulse conduction 23. The direction of cardiac impulse conduction 23 is indicated here by arrows 24. Cardiac impulse conduction 23 is represented in the schematic diagram 21 in a highlighted manner, i.e. for example in color against the background of the image recording 22 represented in gray levels, indicated here by the hatching. In this case, cardiac impulse conduction 23 covers a complete cardiac cycle, i.e. corresponds to the data which is available at the end of a cardiac cycle in relation to the image recording 22.

Alternatively, the respective propagation of cardiac impulse conduction can be shown within the framework of a film, together with an associated anatomical image recording relating to the corresponding point in time of the cardiac cycle, the image recording usefully being effected in an ECG-triggered manner.

The key advantage in the method according to the invention or in using the medical device according to the invention is that cardiac impulse conduction can be recorded or represented comprehensively, in particular three-dimensionally, without a large number of curves being generated whose interpretation is reserved for specialists. By means of the invention, the recording of a vector cardiogram is possible in a simple manner, the method enabling a measurement in the living patient that can be carried out so easily that it can readily be integrated into the clinical routine.

The invention claimed is:

1. A method for determining a cardiac impulse conduction in a patient, comprising:
   arranging a plurality of electrocardiogram electrodes on a body of the patient;
   generating an image recording of an area of the body of the patient by an imaging modality capturing at least partially the electrocardiogram electrodes;
   determining positions of the electrocardiogram electrodes captured in the image recording based on the imaging recording in a system of coordinates assigned to the imaging modality;
   recording potential data of some of the electrocardiogram electrodes captured in the image recording;
   reconstructing the cardiac impulse conduction depending on the positions of the electrocardiogram electrodes, the image recording and the potential data of the electrocardiogram electrodes; and
   displaying the reconstructed cardiac impulse conduction together with the image recording by color,
   wherein the electrocardiogram electrodes are each provided with at least one marking, and
   wherein the at least one marking is different from one another for each of the electrocardiogram electrodes.

2. The method as claimed in claim 1, wherein the image recording is generated substantially simultaneously with the recording of the potential data of the electrocardiogram electrodes or between two recordings of the potential data of the electrocardiogram electrodes.

3. The method as claimed in claim 1, wherein the generation of the image recording is triggered by the recording or an evaluation of the potential data of the electrocardiogram electrodes or is within a framework of image sequences.

4. The method as claimed in claim 1, wherein the imaging modality is selected from the group consisting of: a magnetic resonance device, a computer tomography device, and another X-ray-based device.

5. The method as claimed in claim 1,
   wherein the electrocardiogram electrodes are arranged on a thorax of the patient,
   wherein a three-dimensional model of the thorax of the patient is determined from the image recording, and
   wherein a heart or a surface of the thorax or the positions of the electrocardiogram electrodes in the three-dimensional model of the thorax are automatically determined by a segmenting method.

6. The method as claimed in claim 1,
   wherein a three-dimensional model is generated from the image recording in which tissues of the patient are segmented,
   wherein electrical properties are assigned to the tissues, and
   wherein the cardiac impulse conduction is reconstructed by the three-dimensional model.

7. The method as claimed in claim 1, wherein the cardiac impulse conduction is reconstructed in a vector cardiogram.

8. The method as claimed in claim 1, wherein the display is carried out temporarily or as a function of a user's input.

9. The method as claimed in claim 1, wherein a plurality of image recordings are generated over at least a part of one or more cardiac cycles and a film is generated from the image recordings in which the cardiac impulse conduction is visualized.

10. The method as claimed in claim 1, wherein the marking is composed of a material comprising a unique contrast behavior that is selected from the group consisting of: a metal, a resonance coil, a fluorescent marker, and an X-ray marker.

11. The method as claimed in claim 1, wherein the positions of the electrocardiogram electrodes are determined by a known position of the electrocardiogram electrodes relative to one another.

12. The method as claimed in claim 1, wherein the electrocardiogram electrodes are arranged in a matrix or on a vest.

13. The method as claimed in claim 1, wherein 50 to 200 electrocardiogram electrodes are arranged on the body of the patient.

14. The method as claimed in claim 1, wherein the electrocardiogram electrodes transmit signals wirelessly or using optical waveguides.

15. The method as claimed in claim 1, wherein the reconstructed cardiac impulse conduction is displayed together with the image recording further by an optical highlighting.

16. The method as claimed in claim 1, wherein the at least one marking is different from one another for each of the electrocardiogram electrodes in signal strength, signal length, and signal type.

17. A medical device for determining a cardiac impulse conduction in a patient, comprising:

a plurality of electrocardiogram electrodes that are adapted to be arranged on a body of the patient;

an imaging modality that generates an image recording of an area of the body of the patient capturing at least partially the electrocardiogram electrodes;

a device that records potential data of the electrocardiogram electrodes;

a computing device that:
    determines positions of the electrocardiogram electrodes captured in the image recording based on the imaging recording in a system of coordinates assigned to the imaging modality, and
    reconstructs the cardiac impulse conduction depending on the positions of the electrocardiogram electrodes, the image recording and the potential data of the electrocardiogram electrodes; and a display device that displays the reconstructed cardiac impulse conduction together with the image recording by color, wherein the electrocardiogram electrodes are each provided with at least one marking, and wherein the at least one marking is different from one another for each of the electrocardiogram electrodes.

18. The medical device as claimed in claim 17, wherein the computing device controls the generation of the image recording or the recording of the potential data of the electrocardiogram electrodes or an evaluation of the potential data of the electrocardiogram electrodes.

19. The medical device as claimed in claim 17, wherein the image recording is generated substantially simultaneously with the recording of the potential data of the electrocardiogram electrodes or between two recordings of the potential data of the electrocardiogram electrodes.

* * * * *